United States Patent [19]

Obermeier et al.

[11] Patent Number: 5,473,049

[45] Date of Patent: Dec. 5, 1995

[54] PROCESS FOR OBTAINING PROINSULIN POSSESSING CORRECTLY LINKED CYSTINE BRIDGES

[75] Inventors: Rainer Obermeier, Hattersheim am Main; Martin Gerl, Kriftel/Taunus; Jürgen Ludwig, Brachttal; Walter Sabel, Bad Camberg, all of Germany

[73] Assignee: Hoechst Aktiengesellschaft, Frankfurt, Germany

[21] Appl. No.: 160,376

[22] Filed: Dec. 1, 1993

[30] Foreign Application Priority Data

Dec. 2, 1992 [DE] Germany ............... 42 40 420.7

[51] Int. Cl.⁶ ............... A61K 38/28; C07K 14/62
[52] U.S. Cl. ............... 530/303; 530/324
[58] Field of Search ............... 530/303, 324

[56] References Cited

U.S. PATENT DOCUMENTS

| | | | |
|---|---|---|---|
| 4,430,266 | 2/1984 | Frank | 260/112.7 |
| 4,801,684 | 1/1991 | Grau | 530/303 |
| 5,101,013 | 3/1992 | Dörschug et al. | 530/305 |
| 5,227,293 | 7/1993 | Stengelin et al. | 435/69.7 |

FOREIGN PATENT DOCUMENTS

| | | |
|---|---|---|
| 8179145 | 12/1981 | Australia . |
| 590029 | 5/1987 | Australia . |
| 347781 | 6/1989 | Australia . |
| 611303 | 6/1989 | Australia . |
| 630287 | 4/1991 | Australia . |
| WO9002198 | 3/1990 | WIPO . |
| WOA91/03550 | 7/1993 | WIPO . |

OTHER PUBLICATIONS

Lowe, P., Rhind, S. K., Sugrue, R., Marston, F. A. O. (1987) Protein Purification, Alan Liss Pub., pp. 429–442.
Biochemistry, 60, (1968), S. 622–629.
Jaenicke, R. Rudolph, 1989, "Folding Proteins", *Protein Structure a practical Approach;* ed. Creighton, T.E.S., 191–224, JRL Press Oxford.
Kemmler et al., J. Biol. Chem., 246 (1971), S. 6786.
Chem. Abstract 114:99871s.

*Primary Examiner*—Jill Warden
*Assistant Examiner*—Benet Prickril
*Attorney, Agent, or Firm*—Barbara V. Maurer

[57] ABSTRACT

A process is described for obtaining proinsulin possessing correctly linked cystine bridges from a corresponding proinsulin amino acid chain in the presence of mercaptan and chaotropic auxiliary agents and at a pH of 10 to 11, as well as its direct isolation from the reaction mixture using hydrophobic adsorber resins.

6 Claims, No Drawings

PROCESS FOR OBTAINING PROINSULIN POSSESSING CORRECTLY LINKED CYSTINE BRIDGES

Human insulin is a protein possessing two amino acid chains of 51 amino acid residues in all. 6 cysteine residues are present in the two amino acid chains, with in each case two cysteine residues being linked to each other via a disulfide bridge. In biologically active human insulin, the A and B chains are linked to each other via two cystine bridges, and a further cystine bridge is present in the A chain. From the statistical point of view, there are 15 possibilities of forming disulfide bridges within one human insulin molecule. Only one of the 15 possibilities is present in biologically active human insulin. The following cysteine residues are linked to each other in human insulin:

A 6-A 11

A 7-B 7

A 20-B 19

The letters A or B stand for the respective insulin chains, while the number stands for the position of the amino acid residue, as counted from the amino end to the carboxyl end of the respective amino acid chain. Disulfide bridges can also be formed between two human insulin molecules, so that many different disulfide bridges can readily arise in an unpredictable manner.

A known process for preparing human insulin is based on the use of human proinsulin. Human proinsulin is a protein possessing one linear amino acid chain composed of 86 amino acid residues, with the A and B chains of the human insulin being linked to each other via a C peptide possessing 35 amino acid residues. The formation of the disulfide bridges which are present in human insulin is effected by way of an intermediate, with the cystine residues of the human insulin being provided with a sulfur protective group, e.g. with a S-sulfonate (—S—SO$_3^-$) group (EP 0 037 255). In addition, a process for obtaining proinsulin possessing correctly linked cystine bridges is known (Biochemistry, 60, (1968), pages 622 to 629) for which pig proinsulin is used as the starting material and in which the cystine residues are present as thio residues (—SH). The term "correctly linked cystine bridges" is understood to mean the disulfide bridges which are found in biologically active insulin from mammals.

Recombinant processes make it possible to prepare human proinsulin, or proinsulin possessing an amino acid sequence and/or amino acid chain length diverging from that of human insulin, in microorganisms. The proinsulins which are prepared from recombinantly altered Escherichia coli cells do not possess any correctly linked cystine bridges. A process for obtaining human insulin using E. coli (EP 0 055 945) is based on the following procedural steps:

fermentation of the microorganism—cell disruption—isolation of the fusion protein—cleavage of the fusion protein with cyanogen bromide—isolation of the cleavage product having the proinsulin sequence—protection of the cysteine residues of proinsulin with S-sulfonate groups—formation of the correctly linked cystine bridges—sulfitolysis—desalting of the proinsulin—chromatographic purification of the proinsulin possessing correctly linked cystine bridges—concentration of the proinsulin solution—chromatographic purification of the concentrated proinsulin solution—enzymatic cleavage of the proinsulin in order to obtain human insulin—chromatographic purification of the resulting human insulin.

Disadvantages of this process are the number of procedural steps and the losses in the purification steps, which losses lead to a low yield of insulin. Owing to the multi-step procedural route, substantial losses have to be accepted when using this procedure. From the step of the isolated fusion protein via cyanogen bromide cleavage, sulfitolysis and purification of the proinsulin, a loss of proinsulin of up to 40% is to be expected (EP 0 055 945). High losses of a similar nature can occur during the course of the subsequent purification steps leading to the final product.

Increases in yield in association with the recombinant preparation of human insulin, or of insulin derivatives, can be achieved if the number of the necesary procedural steps can be significantly reduced.

The object of the present invention was to develop a process for obtaining proinsulin possessing correctly linked cystine bridges in the proinsulin amino acid chain, in which process fewer procedural steps are necessary and total purification losses are lower.

A process for obtaining proinsulin of the formula I

FORMULA I

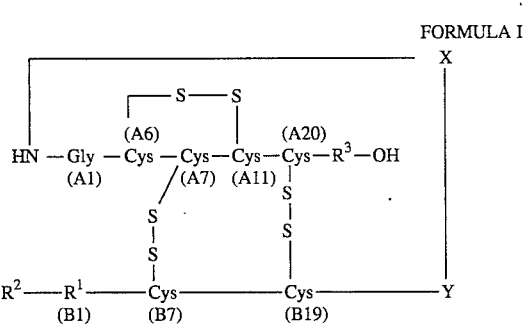

has now been found, which comprises

A) reacting a protein of the formula II,

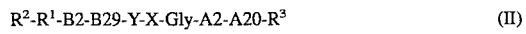

with a quantity of a mercaptan, which quantity yields 2 to 10 —SH radicals of the mercaptan per cysteine residue of the protein of the formula II, in the presence of a chaotropic auxiliary agent in an aqueous medium at a pH of 10 to 11 and at a concentration of the protein of the formula II of 0.05 to 0.3 g per liter of aqueous medium, and the proinsulin of the formula I which is obtained B) being mixed with 3 to 50 g of a hydrophobic adsorber resin per liter of aqueous medium at a pH of 4 to 7, C) the adsorber resin, which has adsorbed proinsulin of the formula I, being isolated, and D) the proinsulin of the formula I being desorbed from the adsorber resin;

in formula I and II

X is a) a genetically encodable amino acid residue or b) a peptide possessing 2 to 35 amino acid residues, Y is a genetically encodable amino acid residue, R$^1$ is a phenylalanine residue or a covalent bond, R$^2$ is a) a hydrogen atom, b) a genetically encodable amino acid residue or c) a peptide possessing 2 to 45 amino acid residues, R$^3$ is a genetically encodable amino acid residue, and the residues A2–A20 correspond to the amino acid sequence of the A chain of human insulin, animal insulin, or an insulin derivative, and the residues B2–B29 correspond to the amino acid sequence of the B chain of human insulin, animal insulin, or an insulin derivative.

Proteins of the formula II are preferred in which

X is a peptide possessing the amino acid sequence of the C chain of human insulin, Y is an amino acid residue selected from the group comprising Ala, Thr or Ser, $R^1$ is the amino acid residue Phe, $R^2$ is a) a hydrogen atom, or b) a peptide possessing 2 to 25 amino acid residues, $R^3$ is an amino acid residue selected from the group comprising Asn, Ser or Gly, and the residues A2–A20 and B2–B29 correspond to the amino acid sequence of the A and B chains of human insulin.

Proteins of the formula II are particularly preferred in which

X is a peptide possessing 2 to 35 amino acid residues, where two basic amino acids, in particular Arg and/or Lys, are located at the beginning and at the end of the peptide, Y is the amino acid residue Thr, $R^1$ is the amino acid residue Phe, $R^2$ is a) a hydrogen atom, or b) a peptide possessing 2 to 15 amino acid residues, at whose carboxyl end the amino acid residue Met or Arg is located, $R^3$ is the amino acid residue Asn, and the residues A2–A20 and B2–B29 correspond to the amino acid sequence of the A and B chains of human insulin.

It has been found, surprisingly, that the protein of the formula II does not have to be completely reduces in a reaction step which customarily precedes refolding (R. Jaenicke, R. Rudolph, 1989, Folding Proteins, in Protein Structure a practical Approach; ed. Creighton, T. E. pp. 191–224, JRL Press Oxford; EP 0 219 874) and that, in the described procedure, despite a high proportion of foreign protein (70–90%), folding yields are achieved which are of comparable magnitude to those achieved when correspondingly purified proinsulin possessing—SH protective groups is folded.

When compared with previously known methods, the process according to the invention makes possible a preparation which is appreciably more rapid and provides higher yields. The reason for this is that the procedural steps of sulfitolysis and, where appropriate, cyanogen bromide cleavage, are avoided and the option, which was previously unknown, is provided for folding proinsulin corresponding to the formula (I) in high yields into the biologically active structure directly from its denatured condition in the presence of limited quantities of chaotropic salts. This makes it possible to separate off the resulting proinsulin from the folding solution by adsorption. Thus, the proinsulins can, following desorption from the adsorbing agent, be used for enzymic conversion to insulin without any prior intermediate isolation or purification. The process according to the invention leads to a substantially abbreviated preparation procedure which, because of shorter standing times and the avoidance of losses, permits increases in yield of the order of 25–100% as compared with the known processes.

The amino acid sequence of peptides and proteins is indicated from the N-terminal end of the amino acid chain. The data given in brackets in formula I, e.g. A6, A20, B1, B7 or B19, correspond to the position of amino acid residues in the A or B chains of the insulin.

The amino acids Gly, Ala, Ser, Thr, Val, Leu, Ile; Asp, Asn, Glu, Gln, Cys, Met, Arg, Lys, His, Tyr, Phe, Trp, Pro and selenocysteine represent the term "genetically encodable amino acid residue".

The terms "residues A2–A20" and "residues B2–B29" of animal insulin are understood to mean, for example, the amino acid sequences of insulin from cattle, pigs or poultry.

The term residues A2–A20 and B2–B29 of insulin derivatives represents the corresponding amino acid sequences of human insulin which are formed by exchanging amino acids for other genetically encodable amino acids.

The A chain of human insulin has the following sequence (SEQ ID NO: 1);

Gly, Ile, Val, Glu, Gln, Cys, Cys, Thr, Ser, Ile, Cys, Ser, Leu, Tyr, Gln, Leu, Glu, Asn, Tyr, Cys, Asn

The B chain of human insulin has the following sequence (SEQ ID NO: 2);

Phe, Val, Asn, Gln, His, Leu, Cys, Gly, Ser, His, Leu, Val, Glu, Ala, Leu, Tyr, Leu, Val, Cys, Gly, Glu, Arg, Gly, Phe, Phe, Tyr, Thr, Pro, Lys, Thr

The C chain of human insulin has the following sequence (SEQ ID NO: 3).

Arg, Arg, Glu, Ala, Glu, Asp, Leu, Gln, Val, Gly, Gln, Val, Glu, Leu, Gly, Gly,
Gly, Pro, Gly, Ala, Gly, Ser, Leu, Gln, Pro, Leu, Ala, Leu, Glu, Gly, Ser, Leu,
Gln, Lys, Arg.

Chaotropic auxiliary agents are compounds which break hydrogen bonds in aqueous solution, for example ammonium sulfate, guanidine hydrochloride, ethylene carbonate, thiocyanate, dimethyl sulfoxide and urea.

The term hydrophobic adsorber resin represents nonionic, hydrophobic, crosslinked polymers and/or copolymers, for example polystyrene or copolymers composed of styrene and divinylbenzene, in particular polymeric adsorber resins having a large surface and many large pores, e.g. commercial preparations from the companies Rohm and Haas or Mitsubishi Chemical Industries Ltd., such as XAD16, XAD1600 or HP20.

The term mercaptan is understood to mean compounds which are soluble in water and contain at least one —SH group. Examples of these compounds are dithiothreitol, dithioerythrol, 2-mercaptoethanol, cysteine, methyl thioglycolate, 3-mercapto-1,2-propanediol and 3-mercaptopropionic acid.

The protein of the formula II can be formed in microorganisms with the aid of a multiplicity of recombinant constructs (EP 0 489 780, EP 0 347 781, EP 0 453 969).

The recombinant constructs are expressed during fermentation in microorganisms such as *Escherichia coli* or streptomycetes. The proteins which are formed are stored within the interior of the microorganisms (EP 0 489 780) or are secreted into the fermentation solution.

For the process according to the invention, proteins of the formula II can be employed which, directly after cell disruption, are still contaminated with a multiplicity of proteins derived from the fermentation solution and from the microorganisms. However, the proteins of the formula II can also be employed in prepurified form, for example following a precipitation or a chromatographic purification.

The approach in procedural step A) is as follows: The proteins are dissolved in a chaotropic auxiliary agent or in mixtures of different chaotropic auxiliary agents. Preferably, guanidine hydrochloride is used at a concentration of 6 to 10M, preferably 8M, based on water as the solvent. The pH of the reaction mixture is 8.5 to 10.8. Examples of buffers which can be used are phosphate, tri(hydroxymethyl)aminomethane(Tris), borate or glycine buffers. The concentration of the buffer substances in the aqueous medium is up to 0.5M, preferably from 0.005M to 0.5M, particularly preferably from 0.05M to 0.1M. Subsequently, the protein mixture is mixed with an aqueous solution of mercaptan. This results in the following concentrations in the reaction solution (based on water):

The concentration of the protein of the formula II is 0.05 to 0.3 g/l, preferably 0.1 to 0.2 g/l.

The quantity of the mercaptan is 2 to 10 —SH radicals of the mercaptan per cysteine residue of the protein of the formula II, preferably 3 to 6.

The pH of the solution is 10 to 11, preferably 10.8. The abovementioned buffer components are used. The precise pH is set by adding sodium hydroxide solution. The concentration of the buffer components is 0.005 to 0.5M, preferably 0.05 to 0.1M.

The concentration of the chaotropic auxiliary agent in the reaction mixture containing the mercaptan is less 1M, preferably 0.1 to 0.8M, in particular 0.3 to 0.6M. Either cysteine or 2-mercaptoethanol on their own, or a mixture of the two, is preferably employed as the mercaptan.

The temperature during the folding in procedural step A) is 0° C. to 50° C., preferably 2° C. to 30° C., in particular 4° C. to 10° C. The reaction time is 3 to 12 hours, preferably 4 to 8 hours, in particular 5 hours.

The product from procedural step A) is a proinsulin of the formula I, which contains correctly linked cystine bridges.

In procedural step B), the reaction solution from procedural step A) is adjusted to a pH of 4 to 7 using an acid such as hydrochloric acid or sulfuric acid. If turbidities arise in the solution, these are removed by filtration or by centrifugation. A hydrophobic adsorber resin is then added to the remaining solution. Resins of the type XAD or HP20 have proved to be suitable. The quantity of the resin is 3 to 50 g per liter of reaction solution, preferably 10 to 25 g/l.

The suspension which is obtained is stirred for 3 to 4 hours. The adsorption of the proinsulin of the formula I to the resin is checked by sampling and by high pressure liquid chromatography analysis (HPLC analysis). As soon as proinsulin can no longer be detected in the solution, the adsorber resin is separated off from the aqueous reaction solution (procedural step C). This is effected, for example, by filtration or centrifugation in accordance with known methods. The resin, with adsorbed proinsulin, is washed with a purely aqueous solution or with a buffer-containing aqueous solution.

The desorption (procedural step D) of the proinsulin of the formula I is effected in accordance with known methods which depend on the hydrophobic adsorber resin used. In the case of XAD or HP20 adsorber resins, for example, desorption is effected using an aqueous solution which contains 10 to 50% of a non-ionic, organic solvent which is miscible with water, e.g. a $(C_1-C_6)$-alkanol. Preferably, 50% isopropanol is used in water as the solvent. The desorption of the proinsulin of the formula I is effected, for example, by washing with the isopropanol solution. The washing can be effected by mixing with the isopropanol solution in a vessel with a stirrer, or by chromatography in a column. The ratio of the volume of resin to that of isopropanol solution is 1:1 to 1:10, preferably 1:1.1 to 1:2. The washing steps can be repeated one to five times, preferably twice. The combined isopropanol fractions can be used for further chromatographic purification or for the enzymic cleavage of the proinsulin to insulin either directly or following dilution with water (Kemmler et al., J. Biol. Chem. 246 (1971), page 6786; EP 0 305 760).

The process according to the invention is described in detail in the following examples. Percentage values relate to weight unless otherwise indicated.

Example 1

Proinsulin 1 possessing the following amino acid sequence is prepared by fermenting genetically modified *Escherichia coli* cells (EP 0 489 780).

Proinsulin 1 (SEQ ID NO: 4);

| Met | Ala | Thr | Thr | Ser | Thr | Gly | Asn | Ser | Ala | Arg | Phe | Val | Asn | Gln | His |
|-----|-----|-----|-----|-----|-----|-----|-----|-----|-----|-----|-----|-----|-----|-----|-----|
| Leu | Cys | Gly | Ser | His | Leu | Val | Glu | Ala | Leu | Tyr | Leu | Val | Cys | Gly | Glu |
| Arg | Gly | Phe | Phe | Tyr | Thr | Pro | Lys | Thr | Arg | Arg | Glu | Ala | Glu | Asp | Leu |
| Gln | Val | Gly | Gln | Val | Glu | Leu | Gly | Gly | Gly | Pro | Gly | Ala | Gly | Ser | Leu |
| Gln | Pro | Leu | Ala | Leu | Glu | Gly | Ser | Leu | Gln | Lys | Arg | Gly | Ile | Val | Glu |
| Gln | Cys | Cys | Thr | Ser | Ile | Cys | Ser | Leu | Tyr | Gln | Leu | Glu | Asn | Tyr | Cys |
| Asn | | | | | | | | | | | | | | | |

Proinsulin 1 corresponds to the formula II, in which

X is the C peptide of human insulin,

Y is Thr (B30), $R^1$ is Phe (B1), $R^2$ is a peptide possessing 11 amino acid residues, $R^3$ is Asn (A21), and A2–A20 is the amino acid sequence of the A chain of human insulin (amino acid residues 2 to 20) and B2–B29 is the amino acid sequence of the B chain of human insulin (amino acid residues 2 to 29).

The expressed proinsulin 1 accumulates in the *E. coli* cells and forms inclusion bodies. Once fermentation is complete, the cells are separated off by centrifugation and disrupted by customary high pressure homogenization. The fusion protein inclusion bodies which are liberated are isolated by centrifugation.

1000 g of the isolated fusion protein inclusion bodies (based on moisture-free weight following freeze drying) of the proinsulin are dissolved in 100 l of an 8M guanidine hydrochloride solution at pH 10.8. After removing small quantities of turbidity-causing solids by centrifugation, the clear solution is stirred into 900 l of an aqueous solution of cysteine (125 g of cysteine hydrochloride hydrate) at a pH of 10.8 and a temperature of 4° C. The insulin content of the fusion protein is determined by SDS electrophoresis scanning (U. K. Lämmli, Nature, Volume 227, pages 680–685, 1970). It is 15%. Following completion of the folding reaction, a proinsulin content of 105 g in the reaction mixture is measured by analytical HPLC.

The solution is adjusted to a pH of 4.5 with 6N HCl and a slight turbidity is removed by centrifugation. 30 kg of HP20 (Mitsubishi Chemical Industries Ltd., Dusseldorf, Germany) are added to the clear solution. The suspension is slowly stirred for about 4 hours until proinsulin 1 can no longer be detected in the supernatant. The resin is separated off by filtration through a suction filter and washed with water. Desorption of the product is effected by slurrying the resin in 50 l of a 50% strength, aqueous, solution of isopropanol. The filtration and the incubation with the isopropanol solution are repeated twice. The yield of proinsulin of the formula I is 103 g.

HPLC analysis 0.5 g of protein is dissolved in 40 ml of a solution composed of 6M guanidine hydrochloride, 50 mM Tris, pH 8.5, 5 mM ethylenediamine tetraacetate (EDTA), 1% 2-mercaptoethanol and 10 mM dithiothreitol at 95° C. for 2 min and then centrifuged at 14000 g for 20 min. 0.02 ml of the clear supernatant is loaded onto a high pressure liquid chromatography column.

Column: ®Nucleogel RP 300-5/46 (Macherey & Nagel, Aachen, Germany)

Gradient: buffer A: 0.1% trifluoroacetic acid (TFA) buffer B: 0.09% TFA in acetonitrile Temperature: 55° C. Total running time: 15 min, The gradient is characterized by the following quantities of buffer B after the corresponding running times:

10 min 25%, 12 min 60%, 13 min 90%, 15 min 100%.

Flow rate: 1 ml/min

Detection: 215 nm

Retention time for proinsulin: 9 min.

Example 2

A proinsulin 2 possessing the following amino acid sequence is prepared by fermenting a genetically modified E. coli (EP 0 347 781):

Proinsulin 2 (SEQ ID NO: 5)

| Met | Ala | Pro | Thr | Ser | Ser | Ser | Thr | Lys | Lys | Thr | Gln | Leu | Gln | Leu | Glu |
| His | Leu | Leu | Leu | Asp | Leu | Gln | Met | Ile | Leu | Asn | Gly | Ile | Asn | Asn | Tyr |
| Lys | Asn | Pro | Lys | Leu | Thr | Arg | Met | Ile | Glu | Gly | Arg | Phe | Val | Asn | Gln |
| His | Leu | Cys | Gly | Ser | His | Leu | Val | Glu | Ala | Leu | Tyr | Leu | Val | Cys | Gly |
| Glu | Arg | Gly | Phe | Phe | Tyr | Thr | Pro | Lys | Thr | Arg | Gly | Ile | Val | Glu | Gln |
| Cys | Cys | Thr | Ser | Ile | Cys | Ser | Leu | Tyr | Gln | Leu | Glu | Asn | Tyr | Cys | Asn |

The expressed proinsulin 2 accumulates in the E. coli cells and frequently forms inclusion bodies. Disruption of the cells is effected as in Example 1. The proinsulins thus obtained are subjected to cleavage with cyanogen bromide, resulting in the formation of proinsulin 3 (SEQ ID NO: 7).

Proinsulin 3 corresponds to the formula II, in which

X is Arg,

Y is Thr (B30), $R^1$ is Phe (B1), $R^2$ is a peptide possessing 4 amino acid residues, $R^3$ is Asn (A21), and A2–A20 and B2–B29 correspond to the amino acid sequences of the A and B chains, respectively, of human insulin.

Following the cleavage with cyanogen bromide, the content of proinsulin 3 in a freeze-dried sample containing 9.2% insulin-containing protein is determined quantitatively by SDS electrophoresis.

1000 g of the proinsulin 3 are incubated together with cysteine hydrochloride hydrate as in Example 1. Following this, a content of 63 g of proinsulin of the formula I in the total reaction mixture is determined using analytical HPLC. As in Example 1, the product is adsorbed with 35 kg of XAD-1600 resin (Rohm and Haas Company, Philadelphia, U.S.A.) and removed from the reaction solution. After washing the resin and desorbing the product, the content of proinsulin of the formula I is determined to be 56 g.

Example 3

Proinsulin 4 possessing the following amino acid sequence is prepared by fermenting a recombinantly modified E. coli (EP 0 489 780):

Proinsulin 4 (SEQ ID NO: 6)

| Met | Ala | Thr | Thr | Ser | Thr | Gly | Asn | Ser | Ala | Arg | Phe | Val | Asn | Gln | His |
| Leu | Cys | Gly | Ser | His | Leu | Val | Glu | Ala | Leu | Tyr | Leu | Val | Cys | Gly | Glu |
| Arg | Gly | Phe | Phe | Tyr | Thr | Pro | Lys | Thr | Arg | Gly | Ile | Val | Glu | Gln | Cys |
| Cys | Thr | Ser | Ile | Cys | Ser | Leu | Tyr | Gln | Leu | Glu | Asn | Tyr | Cys | Asn | |

Proinsulin 4 corresponds to the formula II in which

X is Arg,

Y is Thr, (B30), $R^1$ is Phe (B1), $R^2$ is a peptide possessing 11 amino acids, $R^3$ is Asn (A21), and A2–A20 and B2–B29 correspond to the amino acid sequences of the A and B chains, respectively, of human insulin.

After disrupting the cells, the fusion protein is isolated from the homogenate by centrifugation. Following determination of the content of the product (15%) as in Example 1, 1000 g of the fusion protein are employed for the folding reaction. The folding yield at the end of the reaction is determined, as in Example 1, to be 60%. The yield amounts to 108 g of proinsulin.

We claim:

1. A process for obtaining proinsulin of the formula I

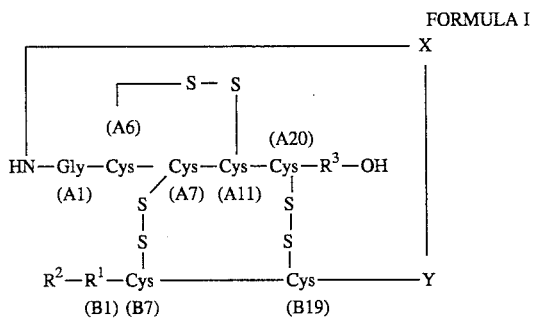

FORMULA I which comprises (A) reacting a protein of the Formula II,

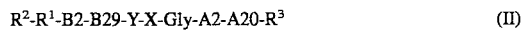

$R^2\text{-}R^1\text{-}B2\text{-}B29\text{-}Y\text{-}X\text{-}Gly\text{-}A2\text{-}A20\text{-}R^3$ (II)

with a quantity of a mercaptan, which quantity yields 2 to 10 —SH radicals of the mercaptan per cysteine residue of the protein of the Formula II, in the presence of at least one chaotropic auxiliary agent in an aqueous medium at a pH of 10 to 11 and at a concentration of the protein of the Formula II of 0.05 to 0.3 g per liter of aqueous medium, and the to form a reaction mixture;

(B) mixing the reaction mixture with 3 to 50 g of a hydrophobic adsorber resin per liter of aqueous medium at a pH of 4 to 7, to form the proinsulin of the Formula I;

(C) isolating the adsorber resin, which has adsorbed proinsulin of the Formula I; and (D) desorbing the proinsulin of the Formula I from the adsorber resin;

wherein in Formula I and II

X is a) a genetically encodable amino acid residue or b) a peptide having 2 to 35 amino acid residues, Y is a genetically encodable amino acid residue, $R^1$ is a phenylalanine residue or a covalent bond, $R^2$ is a) a hydrogen atom, b) a genetically encodable amino acid residue or c) a peptide having 2 to 45 amino acid residues, $R^3$ is a genetically encodable amino acid residue, and the residues A2–A20 correspond to the amino acid sequence of the A chain of human insulin, and the residues B2–B29 correspond to the amino acid sequence of the B chain of human insulin.

2. The process as claimed in claim 1, wherein the protein of the formula II is employed in which X is a peptide having the amino acid sequence of the C chain of human insulin, Y is an amino acid residue selected from the group comprising Ala, Thr or Ser, $R^1$ is the amino acid residue Phe, $R^2$ is a) a hydrogen atom, or b) a peptide having 2 to 25 amino acid residues, $R^3$ is an amino acid residue selected from the group comprising Asn, Ser or Gly, and the residues A2–A20 and B2–B29 correspond to the amino acid sequence of the A and B chains of human insulin.

3. The process as claimed in claim 1, wherein the protein of the formula II is employed in which X is a peptide having 2 to 35 amino acid residues, where two basic amino acids, in particular Arg and/or Lys, are located at the beginning and at the end of the peptide, Y is the amino acid residue Thr, $R^1$ is the amino acid residue Phe, $R^2$ is a) a hydrogen atom, or b) a peptide having 2 to 15 amino acid residues, at whose carboxyl end the amino acid residue Met or Arg is located, $R^3$ is the amino acid residue Asn, and the residues A2–A20 and B2–B29 correspond to the amino acid sequence of the A and B chains of human insulin.

4. The process as claimed in claim 1, wherein cysteine or cysteine hydrochloride hydrate is employed as the mercaptan.

5. The process as claimed in claim 1, wherein a crosslinked polystyrene or copolymer composed of polystyrene and divinylbenzyl is employed as the hydrophobic adsorber resin.

6. The process as claimed in claim 1, wherein the proinsulin of the formula I is desorbed from the adsorber resin using isopropanol.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 21 Amino Acids
        ( B ) TYPE: Amino Acid
        ( D ) TOPOLOGY: Not Relevant ( x i ) SEQUENCE DESCRIPTION: SEQ ID NO: 1:

```
Gly  Ile  Val  Glu  Gln  Cys  Cys  Thr  Ser  Ile  Cys  Ser  Leu  Tyr  Gln  Leu
1                   5                        10                       15
Glu  Asn  Tyr  Cys  Asn
                20
```

( 2 ) INFORMATION FOR SEQ ID NO:2:

( i ) SEQUENCE CHARACTERISTICS:
        ( A ) LENGTH: 30 Amino Acids
        ( B ) TYPE: Amino Acid
        ( D ) TOPOLOGY: Not Relevant ( x i ) SEQUENCE DESCRIPTION: SEQ ID NO: 2:

```
Phe  Val  Asn  Gln  His  Leu  Cys  Gly  Ser  His  Leu  Val  Glu  Ala  Leu  Tyr
1                   5                        10                       15
Leu  Val  Cys  Gly  Glu  Arg  Gly  Phe  Phe  Tyr  Thr  Pro  Lys  Thr
                20                       25                       30
```

( 2 ) INFORMATION FOR SEQ ID NO:3:

( i ) SEQUENCE CHARACTERISTICS:
        ( A ) LENGTH: 35 Amino Acids
        ( B ) TYPE: Amino Acid
        ( D ) TOPOLOGY: Not Relevant ( x i ) SEQUENCE DESCRIPTION: SEQ ID NO: 3:

```
Arg  Arg  Glu  Ala  Glu  Asp  Leu  Gln  Val  Gly  Gln  Val  Glu  Leu  Gly  Gly
1                   5                        10                       15
Gly  Pro  Gly  Ala  Gly  Ser  Leu  Gln  Pro  Leu  Ala  Leu  Glu  Gly  Ser  Leu
                20                       25                       30
Gln  Lys  Arg
         35
```

( 2 ) INFORMATION FOR SEQ ID NO:4:

( i ) SEQUENCE CHARACTERISTICS:
        ( A ) LENGTH: 97 Amino Acids
        ( B ) TYPE: Amino Acid (AA)
        ( D ) TOPOLOGY: Not Relevant ( x i ) SEQUENCE DESCRIPTION: SEQ ID NO: 4:

```
Met  Ala  Thr  Thr  Ser  Thr  Gly  Asn  Ser  Ala  Arg  Phe  Val  Asn  Gln  His
1                   5                        10                       15
Leu  Cys  Gly  Ser  His  Leu  Val  Glu  Ala  Leu  Tyr  Leu  Val  Cys  Gly  Glu
                20                       25                       30
Arg  Gly  Phe  Phe  Tyr  Thr  Pro  Lys  Thr  Arg  Arg  Glu  Ala  Glu  Asp  Leu
```

|    |     |     |     |     | 35  |     |     |     |     | 40  |     |     |     |     | 45  |     |     |     |
|----|-----|-----|-----|-----|-----|-----|-----|-----|-----|-----|-----|-----|-----|-----|-----|-----|-----|-----|

Gln Val Gly Gln Val Glu Leu Gly Gly Gly Pro Gly Ala Gly Ser Leu
 50                      55                60

Gln Pro Leu Ala Leu Glu Gly Ser Leu Gln Lys Arg Gly Ile Val Glu
 65              70                  75                      80

Gln Cys Cys Thr Ser Ile Cys Ser Leu Tyr Gln Leu Glu Asn Tyr Cys
                 85                  90                  95

Asn ( 2 ) INFORMATION FOR SEQ ID NO:5:

( i ) SEQUENCE CHARACTERISTICS:
        ( A ) LENGTH: 96 Amino Acids
        ( B ) TYPE: Amino Acid (AA)
        ( D ) TOPOLOGY: Not Relevant ( x i ) SEQUENCE DESCRIPTION: SEQ ID NO: 5:

Met Ala Pro Thr Ser Ser Ser Thr Lys Lys Thr Gln Leu Gln Leu Glu
 1               5                  10                  15

His Leu Leu Leu Asp Leu Gln Met Ile Leu Asn Gly Ile Asn Asn Tyr
                 20                  25                  30

Lys Asn Pro Lys Leu Thr Arg Met Ile Glu Gly Arg Phe Val Asn Gln
             35                  40                  45

His Leu Cys Gly Ser His Leu Val Glu Ala Leu Tyr Leu Val Cys Gly
 50                  55                  60

Glu Arg Gly Phe Phe Tyr Thr Pro Lys Thr Arg Gly Ile Val Glu Gln
 65              70                  75                      80

Cys Cys Thr Ser Ile Cys Ser Leu Tyr Gln Leu Glu Asn Tyr Cys Asn
                 85                  90                  95

( 2 ) INFORMATION FOR SEQ ID NO:6:

( i ) SEQUENCE CHARACTERISTICS:
        ( A ) LENGTH: 63 Amino Acids
        ( B ) TYPE: Amino Acid (AA)
        ( D ) TOPOLOGY: Not Relevant ( x i ) SEQUENCE DESCRIPTION: SEQ ID NO: 6:

Met Ala Thr Thr Ser Thr Gly Asn Ser Ala Arg Phe Val Asn Gln His
 1               5                  10                  15

Leu Cys Gly Ser His Leu Val Glu Ala Leu Tyr Leu Val Cys Gly Glu
                 20                  25                  30

Arg Gly Phe Phe Tyr Thr Pro Lys Thr Arg Gly Ile Val Glu Gln Cys
             35                  40                  45

Cys Thr Ser Ile Cys Ser Leu Tyr Gln Leu Glu Asn Tyr Cys Asn
 50                  55                  60

( 2 ) INFORMATION FOR SEQ ID NO:7:

( i ) SEQUENCE CHARACTERISTICS:
        ( A ) LENGTH: 56 Amino Acids
        ( B ) TYPE: Amino Acid (AA)
        ( D ) TOPOLOGY: Not Relevant ( x i ) SEQUENCE DESCRIPTION: SEQ ID NO: 7:

Ile Glu Gly Arg Phe Val Asn Gln His Leu Cys Gly Ser His Leu Val
 1               5                  10                  15

Glu Ala Leu Tyr Leu Val Cys Gly Glu Arg Gly Phe Phe Tyr Thr Pro
                 20                  25                  30

```
Lys  Thr  Arg  Gly  Ile  Val  Glu  Gln  Cys  Cys  Thr  Ser  Ile  Cys  Ser  Leu
          35                      40                           45

Tyr  Gln  Leu  Glu  Asn  Tyr  Cys  Asn
     50                  55
```